United States Patent [19]

Budai et al.

[11] Patent Number: 4,727,074
[45] Date of Patent: Feb. 23, 1988

[54] 2-(PHENYLMETHYLENE)-1-(DIAMINOALKOXY) CYCLOALKANES AND THEIR PHARMACEUTICAL USES

[75] Inventors: Zoltan Budai; Tibor Mezei; Aranka Lay nee Konya; Lujza Petócz; Katalin Grasser; Eniko Szirt nee Kiszelly, all of Budapest, Hungary

[73] Assignee: Egyt Gyogyszervegyeszeti Gyar, Budapest, Hungary

[21] Appl. No.: 578,286

[22] Filed: Feb. 8, 1984

[30] Foreign Application Priority Data

Feb. 8, 1983 [HU] Hungary .................. 414/83

[51] Int. Cl.$^4$ .................. A61K 31/495; A61K 31/15; A61K 31/205; C07C 131/02
[52] U.S. Cl. .................. 514/255; 514/554; 514/640; 564/256; 260/501.17
[58] Field of Search .............. 564/256; 424/316, 327; 260/501.15, 501.17; 514/640, 554, 255

[56] References Cited

U.S. PATENT DOCUMENTS 4,077,999  3/1978  Budai et al. .................. 564/256

FOREIGN PATENT DOCUMENTS 169298 of 1977 Hungary.

OTHER PUBLICATIONS

Newbould, B. B. et al. *Br. J. Pharmac.* vol. 35 (1969) pp. 487-497.
Kuhn, W. L. et al. *J. Pharm. Exptl. Ther.* vol. 134 (1961) pp. 60-68.
Marmo, E. et al. *Arzneimittelforschung* vol. 20 (1970) pp. 1-18.
Litchfield, J. T. et al. *J. Pharmacol. Exp. Ther.* vol. 96 (1949) pp. 99-113.
Marmo, Von E. et al. *Arzneimittel-Forschung* vol. 20 (1970) pp. 3-18.
Rudiger, Heinz Jurgen et al. *Naunym-Schmiedeberg's Arch Pharmacol* (1981) vol. 317 pp. 238-244.

*Primary Examiner*—Donald B. Moyer
*Assistant Examiner*—L. Hendriksen
*Attorney, Agent, or Firm*—Keil & Weinkauf

[57] ABSTRACT

The invention relates to selected stereoisomers having the E, E or E, Z configuration and within the Formula (I)

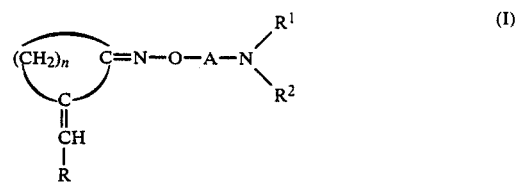

wherein N is 2-4, A is alkylene or 2 or 3 carbon atoms, R is phenyl or substituted phenyl and $R^1$ and $R^2$ are lower alkyl, or, together with the carbon to which attached, form a heterocyclic ring; and pharmaceutically acceptable acid addition salts thereof, a process for their preparation and pharmaceutical compositions comprising the same.

The compounds of the general formula (I) can be used in therapy due to their narcosis potentiating, analgesic and antiarrhytmial effect.

6 Claims, No Drawings

2-(PHENYLMETHYLENE)-1-(DIAMINOALKOXY) CYCLOALKANES AND THEIR PHARMACEUTICAL USES

This invention relates to basic oxim ethers a process for the preparation thereof, pharmaceutical compositions comprising the same and the use thereof in therapy. More particularly the present invention is directed to new basic oxime ethers having narcosis potentiating, analgesic and/or antiarrhythmial effect.

In the Hungarian patent specification No. 169,298 basic oxime ethers having local anaesthetic, spasmolytic, antiparkinson, antiepileptic and antidepressant effect are described. According this patent the said compounds can be prepared either by reacting the corresponding ketone or thione with an amino alkyl hydroxylamine derivative or by reacting the corresponding oxime with a halogeno alkyl amine derivative and aminating the halogeno derivative thus obtained.

It has been found according to the present invention that certain new basic oxim ethers which fall under the general Formula of Hungarian Pat. No. 169,298 but are actually not disclosed therein possess a spectrum of effect being significantly different from that of the compounds disclosed in the said Hungarian patent specification. The new compounds of the present invention exhibit a significant narcosis potentiating and analgesic effect in addition to a favourable antiarrhytmical effect and simultaneously the reserpine antagonistic effect being characteristic of the antidepressant effect practically disappears. In Hungarian patent specification No. 169,298 there is no disclosure of any narcosis potentiating, analgesic and antiarrhythmial effect of the compounds.

According to a feature of the present invention there are provided new basic oxime ethers of the general Formula (I)

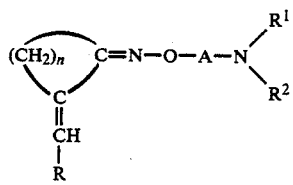

and pharmaceutically acceptable acid addition salts thereof
(wherein
  (A) if n is 4,
    ($A_1$) R stands for phenyl, A is trimethylene and $R^1$ and $R^2$ each stand for isopropyl or together with the adjacent nitrogen atom form a N-phenyl-piperazino group; or
    ($A_2$) R stands for phenyl, A is ethylene and $R^1$ and $R^2$ each stand for isopropyl; or
    ($A_3$) R stands for phenyl, A is —$CH_2$—$CH(CH_3)$— and $R^1$ and $R^2$ each stand for methyl; or
    ($A_4$) R stands for 4-chloro-phenyl, A is trimethylene and $R^1$ and $R^2$ each represent isopropyl; or
    ($A_5$) R stands for 4-chloro-phenyl, A is ethylene and $R^1$ and $R^2$ each stand for methyl; or
  (B) if n is 5,
    ($B_1$) R stands for phenyl, A is ethylene and $R^1$ and $R^2$ are identical and each stand for methyl or isopropyl; or
    ($B_2$) R stands for phenyl, A is —$CH_2$—$CH(CH_3)$— and $R^1$ and $R^2$ are methyl; or
    ($B_3$) R stands for 3-chloro-phenyl, A is trimethylene and $R^1$ and $R^2$ together with the adjacent nitrogen atom form a N-benzylpiperazino group; or
  (C) if n is 6,
    ($C_1$) R stands for phenyl, A is trimethylene and $R^1$ and $R^2$ each stand for methyl; or
    ($C_2$) R stands for phenyl, A is ethylene and $R^1$ and $R^2$ each stands for isopropyl;
with the proviso that if n is 5 and R is phenyl and A is ethylene and $R^1$ and $R^2$ each are isopropyl, the compound of the general Formula (I) is of Z,E configuration and in all the other cases the compound of the general Formula (I) is of E,E configuration).

The acid addition salts of the compounds of the general Formula (I) may be addition salts formed with pharmaceutically acceptable inorganic or organic acids, e.g. hydrochlorides, hydrobromides, sulfates, phosphates, acetates, propionates, methane sulfonates, p-toluene-sulfonates, tartarates, succinates, maleates, fumarates, citrates, malates, lactates etc..

The following compounds of the general Formula (I) possess particularly valuable pharmaceutical properties:
2-[(E)-phenylmethylene]-1-[(E)-(3'-diisopropylamino-propoxyimino]-cyclohexane;
2-[(E)-(p-chloro-phenylmethylene)]-1-[(E)-(3'-diiso-propylamino-propoxyimino)]-cyclohexane
and pharmaceutically acceptable acid addition salts thereof.

According to a further feature of the present invention there is provided a process for the preparation of compounds of the general Formula (I) (wherein
  (A) if n is 4,
    ($A_1$) R stands for phenyl, A is trimethylene and $R^1$ and $R^2$ each stand for isopropyl or together with the adjacent nitrogen atom form a N-phenylpiperazino group; or
    ($A_2$) R stands for phenyl, A is ethylene and $R^1$ and $R^2$ each stand for isopropyl; or
    ($A_3$) R stands for phenyl, A is —$CH_2$—$CH(CH_3)$— and $R^1$ and $R^2$ each stand for methyl; or
    ($A_4$) R stands for 4-chloro-phenyl, A is trimethylene and $R^1$ and $R^2$ each represent isopropyl; or
    ($A_5$) R stands for 4-chloro-phenyl, A is ethylene and $R^1$ and $R^2$ each stand for methyl; or
  (B) if n is 5,
    ($B_1$) R stands for phenyl, A is ethylene and $R^1$ and $R^2$ are identical and each stand for methyl or isopropyl; or
    ($B_2$) R stands for phenyl, A is —$CH_2$—$CH(CH_3)$— and $R^1$ and $R^2$ are methyl; or
    ($B_3$) R stands for 3-chloro-phenyl, A is trimethylene and $R^1$ and $R^2$ together with the adjacent nitrogen atom form a N-benzylpiperazino group; or
  (C) if n is 6,
    ($C_1$) R stands for phenyl, A is trimethylene and $R^1$ and $R^2$ each stand for methyl; or
    ($C_2$) R stands for phenyl, A is ethylene and $R^1$ and $R^2$ each stand for isopropyl;
with the proviso that if n is 5 and R is phenyl and A is ethylene and $R^1$ and $R^2$ each are isopropyl, the compound of the general Formula (I) is of Z,E configuration and in all the other cases the compound of the general Formula (I) is of E,E configuration), and pharmaceutically acceptable acid addition salts thereof, which comprises (a) reacting a compound of the general Formula (II)

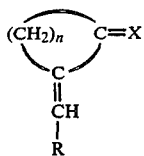   (II)

with a compound of the general Formula (III)

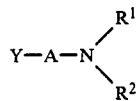   (III)

or an acid addition salt thereof (wherein either X stands for oxygen or sulfur and Y represents an aminooxy group of the Formula $H_2N-O-$ or X stands for a hydroxyimino group of the Formula $=N-OH$ and Y represents halogen and R, n, A, $R^1$ and $R^2$ are as stated above); or (b) reacting a compound of the general Formula (II) with a halogeno compound of the general Formula (IV)

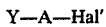   (IV)

and treating the compound of the general Formula (V)

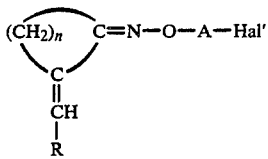   (V)

thus obtained with an amine of the general Formula (VI)

   (VI)

or an acid addition salt thereof (wherein Y, X, R, n, $R^1$, $R^2$, A and n are as stated above and Hal' is halogen) and if desired converting the compound of the general Formula (I) obtained by process (a) or (b) into a pharmaceutical acceptable acid addition salt thereof or setting free the base from a salt.

The term "halogen" encompasses the fluorine, chlorine, bromine and iodine atoms.

According to an embodiment of process (a) a compound of the general Formula (II), wherein X stands for oxygen or sulfur, is reacted with a compound of the general Formula (III) in which Y is an aminooxy group of the Formula $H_2N-O-$. The reaction is preferably carried out in the presence of a basic condensing agent, such as organic amines (e.g. pyridine, picoline or lutidine etc). The reaction may be accomplished in an inert organic solvent. As reaction medium preferably aromatic hydrocarbons (e.g. benzene or toluene) or aliphatic alcohols (e.g. methanol or ethanol) may be used. The reaction may be carried out at a temperature between 20° C. and the boiling point of the reaction mixture, preferably at 40°–80° C. The hydroxyamine derivative of the general Formula (III) may also be used in the form an acid addition salt thereof; the hydrochlorides can be particularly advantageously applied.

According to an other embodiment of process (a) of the present invention a compound of the general Formula (III), wherein X stands for a hydroxyimino group of the Formula $=NOH$, is reacted with a compound of the general Formula (III), in which Y is halogen. This reaction may be preferably carried out in the presence of a basic condensing agent. For this purpose alkali amides (e.g. sodium or potassium amide), alkali hydrides (e.g. sodium or potassium hydride), alkali alcoholates (e.g. sodium methylate, sodium ethylate or potassium tert.butylate) or alkali hydroxides (e.g. sodium or potassium hydroxide) may be used. The reaction may be carried out in an inert organic solvent. The reaction medium depends on the basic condensing agent used. If alkali amides or alkali hydrides are used, the reaction may be carried out in an aromatic hydrocarbon (e.g. benzene or toluene). If an alkali alcoholate is used as basic condensing agent, the alcohol corresponding to the alcoholate may preferably serve a reaction medium. If alkali hydroxides are used as basic condensing agent, the reaction may be preferably carried out in aqueous medium. The halogeno alkyl amine of the general Formula (III) may also be used in the form of an acid addition salt, particularly as the hydrochloride. The reaction may be accomplished at a temperature between 20° C. and the boiling point of the reaction mixture, preferably at 30°–60° C.

In the first step of process (b) a compound of the general Formula (II) is reacted with a halogeno derivative of the general Formula (IV). The reaction may be preferably carried out in the presence of a basic condensing agent. For this purpose e.g. alkali amides (e.g. sodium or potassium amide), alkali hydrides (e.g. sodium or potassium hydride) or alkali metals may be used. The reaction may be preferably accomplished in an inert organic solvent. The reaction medium depends on the basic condensing agent used. If alkali amides or alkali hydrides are used as basic condensing agent, preferably aromatic hydrocarbons (e.g. benzene, toluene, xylene or cumol) may serve as reaction medium. If an alkali metal is used as basic condensing agent, the reaction may be preferably carried out in a lower aliphatic alcohol (e.g. methanol or ethanol etc.).

In the second step of process (b) the compound of the general Formula (V) formed is reacted with an amine of the general Formula (VI) or an acid addition salt thereof. Amination is preferably carried out under pressure in an autoclave.

The isolation and purification of the compounds of the general Formula (I) may be carried out by methods known per se.

The compounds of the general Formula (I) can be converted into their acid addition salts by methods known per se. Salt formation may be carried out preferably in an inert organic solvent.

The starting materials used in the process of the present invention are known or can be prepared by methods analogous to those disclosed in Hungarian patent specification No. 169,298.

The compounds of the general Formula (I) possess valuable narcosis potentiating, antianginal, analgesic and antiarrhythmial properties. The pharmacological activity of the new compounds of the present invention is demonstrated by the following standard tests.

(1) Acute toxicity on mice

The acute toxicity is determined on male and female white mice of the CFLP strain. The body weight of the animals amounts to 18-24 g. The test compound is administered orally in a dose of 20 ml/kg. After treatment the animals are placed in a mouse box and kept on scrapings litter at room temperature. The animals receive mouse fodder and tap water ad libitum. After treatment the animals are observed for a period of 4 days and the toxicity data are determined by the graphic method.

(2) Narcosis potentiating effect

To mice having a body weight of 20-24 g Hexobarbital is administered intravenously in a dose of 40 ml/kg. The sleeping time of the treated and control animals is measured. The test compounds are considered to exhibit narcosis potentiating effect if the average sleeping time of the treated animals becomes 2.5 times longer than that of the average value of the control group. The $ED_{50}$ values are calculated on the basis of these data. The results obtained are summarized in Table I.

TABLE I

| Narcosis potentiating effect on mice | | | |
|---|---|---|---|
| Test compound | $LD_{50}$ mg/kg | $ED_{50}$ mg/kg | Therapeutical index |
| Example No. | | | |
| 13 | 2000 | 10 | 200.0 |
| 5 | 800 | 40 | 20.0 |
| 11 | 1000 | 2 | 500.0 |
| 9 | 600 | 23 | 26.0 |
| 8 | 800 | 22 | 36.4 |
| 1 | 2000 | 200 | 10.0 |
| Meprobamate | 1100 | 260 | 4.2 |
| Reference compound A | inactive in a dose of 50 mg/kg | | |
| Reference compound B | inactive in a dose of 140 mg/kg | | |
| Reference compound C | inactive in a dose of 100 mg/kg | | |
| Reference compound D | inactive in a dose of 320 mg/kg | | |
| Reference compound E | inactive in a dose of 170 mg/kg | | |

It appears from the above Table I that the new compounds of the present invention exhibit a significantly stronger narcosis potentiating effect than the commercially available Meprobamate. On the other hand, the known compounds specifically disclosed in Hungarian Pat. No. 169,298 do not exert any narcosis potentiating effect in the used dosage.

(3) Analgesic effect on mice

To mice 0.4 ml of 0.5% acetic acid is intravenously administered. After 5 minutes the characteristic writhing reactions are counted for a period of 5 minutes. The test compound is administered orally one hour prior to the administration of acetic acid. The activity is expressed in the percentage of the data obtained for the control group. The results are disclosed in Table II.

TABLE II

| Analgesic effect on mice | | | |
|---|---|---|---|
| Test compound | $LD_{50}$ mg/kg | $ED_{50}$ mg/kg | Therapeutical index |
| Example No. | | | |
| 2 | 740 | 43 | 17.2 |
| 3 | 1100 | 45 | 24.2 |
| 1 | >2000 | 200 | >10.0 |
| 11 | 1000 | 150 | 6.7 |
| 10 | 400 | 58 | 6.9 |
| Paracetamol | 510 | 180 | 2.8 |
| Reference compound F | 1750 | inactive in a dose of 350 mg/kg | |
| Reference compound A | 250 | inactive in a dose of 50 mg/kg | |
| Reference compound G | 325 | inactive in a dose of 65 mg/kg | |

Table II shows that the analgesic effect of the new compounds of the general Formula (I) is several times stronger than that of the commercially available Paracetamol. On the other hand, the known compounds specifically disclosed in Hungarian Pat. No. 169,298 do not possess analgesic properties.

(4) Antiarrhythmial effect on rats

The antiarrhythmial effect is determined on rats (both male and female; body weight 160-200 g) according to the modified test of Marmo et al. [Marmo et al.: Arzneimittelforschung 20, 12 (1970)]. Aconitine is intravenously administered in the form of a bolus injection. The ECG deviations are followed for 5 minutes by a standard II method. The test compound is administered intravenously 2 minutes before the addition of aconitine. The test results are summarized in Table III.

TABLE III

| Antiarrhythmial effect on rats | | |
|---|---|---|
| Test compound | Dose mg/kg i.v. | Percental inhibition of aconitine |
| 6 | 1 | 86.2 |
| 12 | 2 | 39.2 |
| 13 | 2 | 35.3 |
| 5 | 4 | 34.7 |
| 10 | 4 | 57.6 |
| Lidocaine | 4 | 23.5 |

The data of Table III show that the new compounds of the present invention possess a stronger antiarrhythmial effect than Lidocain. This effect appears both at intravenous and peroral administration.

In Table IV the antiarrhythmial effect of a representative compound of the present invention is compared to that of a very active compound specifically disclosed in Hungarian Pat. No. 169,298. The test is carried out as disclosed in connection with Table III.

TABLE IV

| Antiarrhythmial effect on rats | | | |
|---|---|---|---|
| Test compound | $LD_{50}$ mg/kg i.v. | Percental aconitine inhibition $ED_{50}$ mg/kg | Therapeutical index |
| Example 4 | 12.50 | 0.54 | 23.14 |
| Reference compound G | 21.19 | 2.00 | 10.59 |

The above data prove that the new compound of the present invention is superior to the known derivative both in respect of the absolute dose and the therapeutical index.

In the above tests the following reference compounds are used:

Meprobamate=2-methyl-2-n-propyl-1,3-propanediol-dicarbamate;

Paracetamol=4-hydroxy-acetanilide;

Lidocain=N,N-diethyl-2,6-dimethyl-acetanilide;

Referent compound A=2-benzyl-1-(3'-dimethylamino-propoxy-imino)-cyclohexane (Example 34 of Hungarian Pat. No. 169,298);

Reference compound B=1-[2'-methyl-3'-(4''-methyl-piperazinyl)-propoxyimino]-2-(p-methoxy-benzyl)-cyclohexane (Example 26 of Hungarian patent No. 169,298);

Reference compound C=1-(2'-methyl-3'-dimethylaminopropoxyimino)-2-(o-methoxy-benzal)-cyclohexane (Example 21 of Hungarian Pat. No. 169,298);

Reference compound D=2-(p-chloro-benzyl)-1-[3'-(4''-methyl-piperazinyl)-propoxyimino]-cyclohexane (Example 44 of Hungarian Pat. No. 169,298);

Reference compound E=1-(3'-dimethylamino-propoxyimino)-2-(p-chlorobenzyl)-cyclohexane (Example 45 of Hungarian Pat. No. 169,298);

Reference compound F=1-(3'-dimethylamino-propoxyimino)-2-(p-methoxybenzal)-cyclohexane (Example 41 of Hungarian Pat. No. 169,298);

Reference compound G=2-benzal-1-(2'-diisopropylamino-ethoxyimino)-cycloheptane (Example 14 of Hungarian Pat. No. 169,298).

According to a further feature of the present invention there are provided pharmaceutical compositions having particularly narcosis potentiating, analgesic, antianginal, and/or antiarrhythmial effect comprising as active ingredient a compound of the general Formula (I) (wherein the substituents have the same definition as described above) or a pharmaceutically acceptable acid addition salt thereof in admixture with inert, usual, solid or liquid carriers. The pharmaceutical compositions may be finished in forms suitable for oral (e.g. tablets, pills, coated pills, dragées, capsules) or parenteral (e.g. injectable solutions) administration. As inert carrier e.g. starch, magnesium stearate, polivinylpyrrolidone, talc, calcium carbonate, lactose, polypropylene glycol etc. may be used.

The pharmaceutical compositions of the present invention can be prepared by methods of the pharmaceutical industry known per se by admixing the active ingredient with suitable inert carriers and, if necessary, other additives and finishing the mixture in forms ready for direct medical use.

According to a further feature of the present invention there is provided the use of the compounds of the general Formula (I) and pharmaceutically acceptable acid addition salts thereof in therapy, particularly as narcosis potentiating, analgesic and/or antiarrhythmial agents.

According to a still further feature of the present invention there is provided a process for narcosis potentiating and for the treatment and prophylaxis of pain and arrhythmia in humans by administering pharmaceutical compositions of the present invention to the patients.

Further details of the present invention are to be found in the Examples without limiting the scope of protection to the said Examples.

EXAMPLE 1

Preparation of 2-[(E)-phenylmethylene]-1-[(E)-(4'-phenyl-piperazinyl-propoxyimino)]-cyclohexane Into an apparatus equipped with a stirrer 50 ml of water, 40 g of sodium hydroxide and 10 g of potassium hydroxide are weighed in. After complete dissolving a solution of 20.1 g (0.1 mole) of 2-(E)-phenylmethylene-cyclohexane-1-one-(E)-oxide in 30 ml of dimethyl sulfoxide is added whereupon 32.73 g (0.105 mole) of N-phenyl-N'-(3-chloropropyl)-piperazine-dihydrochloride are administered in several portions. During the addition the temperature rises to 50°–55° C. The reaction mixture is subjected to post-reaction at room temperature for some hours, poured into 150 g of ice cold water and extracted with benzene. Thus 33.09 g of the desired compound are obtained, yield 82%. The hydrochloride melts at 189.5°–193.5° C.

Analysis for the Formula $C_{26}H_{34}ClN_3O$ (440.04): calc.: C %=70.97, H %=7.79, Cl %=8.06, N %=9.55; found: C %=70.97, H %=7.98, Cl %=7.94, N %=9.46.

EXAMPLE 2

Preparation of 2-[(E)-(m-chloro-phenylmethylene)]-1-[(E)-(4'-benzyl-piperazinyl-propoxyimino)]-cycloheptane Into the apparatus described in Example 1 50 ml of water and 50 g of potassium hydroxide are weighed in. After complete dissolving 24.97 g (0.1 mole) of 2-[(E)-(m-chloro-phenylmethylene)]-cycloheptane-1-one-(E)-oxime in 25 ml of acetonitrile are added. After post-reaction at 60° C. for an hour 35.72 g (0.11 mole) of N-benzyl-N'-(3-chloropropyl)-piperazine-dihydrochloride are added in small portions. After the addition is completed the reaction mixture is subjected to post-reaction at 60° C. for some hours, poured onto 100 g of crushed ice, extracted with dichloro ethane and the organic phase is evaporated. Thus 36 g of the desired compound are obtained, yield 79.8%. The 2-(E)-butenedioate (½) melts at 196°–199° C.

Analysis for the Formula $C_{35}H_{42}ClN_3O$ (684.20): calc.: C %=61.44, H %=6.18, Cl %=5.18, N %=6.14; found: C %=61.58, H %=6.34, Cl %=5.21, N %=6.24.

U.V.: $\lambda_{max}$=274 nm ($\epsilon$=137006)

EXAMPLE 3

Preparation of 2-[(E)-(p-chloro-phenylmethylene)]-1-[(E)-(3'-diisopropylamino-propoxyimino)]-cyclohexane Into an apparatus equipped with a stirrer 50 ml of water, 40 g of sodium hydroxide and 10 g of potassium hydroxide are weighed in. After complete dissolving a solution of 23.57 g (0.1 mole) of 2-[(E)-(p-chlorophenylmethylene)]-cyclohexane-1-one-(E)-oxime in 30 ml of dimethyl sulfoxide and 15.65 g (0.1 mole) of 1-bromo-3-chloro-propane are added at 50°–60° C. The reaction mixture is allowed to stand at this temperature for some hours. The upper oily phase is separated (weight: 26.5 g), 100 ml of dimethyl formamide and 20.2 g (0.2 mole) of N,N-diisopropyl amine are added. The mixture is stirred at 100° C. for 5 hours, poured onto 200 g of icecold water, extracted with benzene, the benzene layer is washed neutral and evaporated. Thus 32.05 g of the desired compound are obtained in the form of a faint yellow oil, yield 85%. The 2-(E)-butenedioate (1/1) melts at 87°–89.5° C. Analysis for the Formula $C_{26}H_{37}ClN_2O_5$ (493.06): calc.: C %=63.34, H %=7.56, Cl %=7.19, N %=5.68; found: C %=63.28, H %=7.6, Cl %=7.15, N %=5.63.

U.V.: $\lambda_{max}=280$ nm ($\epsilon=17456$)

The melting point of the 2-(E)-butenedioate/water (1/1/1) salt amounts to 117°–119° C.

Analysis for the Formula $C_{26}H_{39}ClN_2O_6$ (511.05): calc.: C %=61.10, H %=7.69, Cl %=6.94, N %=5.48; found: C %=61.15, H %=7.73, Cl %=6.95, N %=5.43.

EXAMPLE 4

Preparation of
2-[(E)-phenylmethylene]-1-[(E)-(3'-diisopropylamino-propoxyimino)]-cyclohexane One proceeds according to Example 3 except that 20.13 g (0.1 mole) of 2-(E)-phenylmethylene-cyclohexane-1-one-(E)-oxime are used as starting material. Thus 28.47 g of the desired compound are obtained, yield 83.1%. The 2-(E)-butenedioate (1/1) salt melts at 129°–131° C.

Analysis for the Formula $C_{26}H_{38}N_2O_5$ (458.61): calc.: C %=68.09, H %=8.35, N %=6.10; found: C %=67.94, H %=8.47, N %=6.15.

U.V.: $\lambda_{max}=275$ nm ($\epsilon=14196$)

EXAMPLE 5

Preparation of
2-[(Z)-phenylmethylene]-1-[(E)-(2'-diisopropylamino-ethoxyimino)]-cycloheptane Into an apparatus equipped with a stirrer 21.53 g (0.1 mole) of 2-(Z)-phenylmethylene-cycloheptane-1-one-(E)-oxime and 22.02 g (0.11 mole) of 1-diisopropylamino-2-chloro-ethane-hydrochloride are weighed in. To the mixture 150 ml of xylene and 18.9 g (0.35 g) of sodium methylate are added, the stirrer is started and 30 ml of a mixture of xylene and methanol are distilled off under atmospheric pressure. The reaction mixture is stirred to boiling for some hours, poured onto 200 g of crushed ice, the xylene phase is separated and evaporated. Thus 31.3 g of the desired compound are obtained in the form of a faint yellow oil, yield 91.4%. The 2-(E)-butenedioate (1/1) salt melts at 117°–° C.

Analysis for the Formula $C_{26}H_{38}N_2O_5$ (458.6): calc.: C %=68.09, H %=8.35, N %=6.11; found: C %=67.92, H %=8.42, N %=6.07.

U.V.: $\lambda_{max}=258$ nm ($\epsilon=11182$)

EXAMPLE 6

Preparation of
2-[(E)-phenylmethylene]-1-[(E)-(3'-diisopropylamino-propoxyimino)]-cyclohexane One proceeds according to Example 1 except that 20.13 g (0.1 mole) of 2-(E)-phenylmethylene-cyclohexane-1-one-(E)-oxime and 23.55 g (0.11 mole) of 1-diisopropylamino-3-chloro-propane-hydrochloride are used as starting material. Thus 31.99 g of the desired compound are obtained, yield 93.4%. The 2-(E)-butene-dioate (1/1) melts at 128.5°–131.5° C.

Analysis for the Formula $C_{26}H_{38}N_2O_5$ (458.61): calc.: C %=68.09, H %=8.35, H %=6.10; found: C %=68.28, H %=8.35, H %=6.28.

U.V.: $\lambda_{max}=275$ nm ($\epsilon=14196$)

EXAMPLE 7

Preparation of
2-[(E)-(p-chloro-phenyl-methylene)]-1-[(E)-(3'-diisopropyl-amino-propoxyimino)]-cyclohexane One proceeds according to Example 1 except that 23.57 g (0.1 mole) of 2-(E)-(p-chloro-phenylmethylene]-cyclohexane-1-one-(E)-oxime and 23.55 g (0.11 mole) of 1-diisopropylamino-3-chloro-propane.HCl are used as starting material. Thus 35.63 g of the desired compound are obtained, yield 94.5%. The 2-(E)-butenedioate (1/1) melts at 87°–89.5° C.

Analysis for the Formula $C_{26}H_{37}ClN_2O_5$ (493.06): calc.: C %=63.34, H %=7.56, Cl %=7.19, N %=5.68; found: C %=63.30, H %=7.54, Cl %=7.13, N %=5.60.

U.V.: $\lambda_{max}=280$ nm ($\epsilon=17456$)

EXAMPLE 8

Preparation of
2-[(E)-phenylmethylene]-1-[(E)-(2'-dimethylamino-2'-methyl-1-ethoxyimino)]-cycloheptane To a suspension of 2.4 g (0.1 mole) of sodium hydride in 50 ml of anhydrous toluene a solution of 21.53 g (0.1 mole) of 2-(E)-phenylmethylene-cycloheptane-1-one-(E)-oxime and 200 ml of anhydrous toluene is added dropwise under constant stirring at 85° C. The mixture is heated to boiling for 2 hours whereupon a solution of 16.6 g (0.105 mole) of 2-dimethylamino-2-methyl-1-chloro-ethane and 30 ml of anhydrous toluene is added. The reaction mixture is heated to boiling for further 6 hours, cooled to 30° C., washed with 100 ml of water and extracted with an aqueous solution of 15 g (0.1 mole) of tartaric acid (or with a 0.15 molar diluted aqueous hydrochloric acid solution). The aqueous phase is made alkaline to the pH value of 10 ammonium hydroxide, the separated oily base is extracted with dichloro ethane and the solvent is distilled off. Thus 20.49 g of the desired compound are obtained in the form of a faint yellow oil, yield 68.2%. The 2-(E)-butene-dioate (1/1) melts at 121°–123° C.

Analysis for the Formula $C_{23}H_{32}N_2O_5$ (416.51): calc.: C %=66.32, H %=7.75, N %=6.73; found: C %=66.48, H %=7.95, N %=6.70.

U.V.: $\lambda_{max}=262$ nm ($\epsilon=17595$)

EXAMPLE 9

Preparation of
2-[(E)-phenylmethylene]-1-[(E)-(2'-dimethylamino-2'-methyl-1-ethoxyimino)]-cyclohexane One proceeds according to Example 2 except that 20.13 g (0.1 mole) or 2-(E)-phenylmethylene-cyclohexane-1-one-(E)-oxime and 16.6 g (0.105 mole) of 2-dimethylamino-2-methyl-1-chloro-ethane are used as starting material. Thus 26.9 g of the desired compound are obtained, yield 93.9%. The 2-(E)-butene-dioate salt (1/1) melts at 113°–117° C.

Analysis for the formula $C_{22}H_{30}N_2O_5$ (402.48): calc.: C %=65.64, H %=7.51, N %=6.96; found: C %=65.98, H %=7.60, N %=7.00.

U.V.: $\lambda_{max}=273$ nm ($\epsilon=13475$)

EXAMPLE 10

Preparation of
2-[(E)-phenylmethylene]-1-[(E)-(2'-diisopropylamino-ethoxyimino)]-cyclooctane One proceeds according to Example 5 except that 22.93 g (0.1 mole) of 2-(E)-phenylmethylene-cyclooctane-1-one-(E)-oxime and 22.02 g (0.11 mole) of 1-diisopropylamino-2-chloro-ethane are used as starting material. Thus 33.22 g of the desired compound are obtained, yield, 93.2%. The hydrochloride melts at 159°–161° C.

Analysis for the Formula $C_{27}H_{37}ClN_2O$ (393.0): calc.: C %=70.29, H %=9.47, Cl %=9.02, N %=7.13; found: C %=69.78, H %=9.32, Cl %=9.11, N %=7.32.

U.V.: $\lambda_{max}$=276 nm ($\epsilon$=14170)

EXAMPLE 11

Preparation of
2-[(E)-phenylmethylene)]-1-[(E)-(3'-dimethylamino-propoxyimino)]-cyclooctane One proceeds according to Example 8 except that 22.93 g (0.1 mole) of 2-(E)-phenylmethylene-cyclooctane-1-one-(E)-oxime and 17.39 g (0.1 mole) of 1-dimethylamino-3-chloro-propane.HCl are used as starting material and 3.9 g (0.1 mole) of sodium amide are added. Thus 19.14 g of the desired compound are obtained, yield 63.7%. The 2-(E)-butene-dioate melts at 136°–139° C.

Analysis for the Formula $C_{23}H_{32}N_2O_5$ (416.52): calc.: C %=66.32, H %=7.75, N %=6.73; found: C %=66.74, H %=7.96, N %=6.65.

U.V.: $\lambda_{max}$=276 nm ($\epsilon$=14395)

EXAMPLE 12

Preparation of
2-[(E)-phenylmethylene)]-1-[(E)-(2'-diisopropylamino-ethoxy-imino)]-cyclohexane One proceeds according to Example 2 except that 20.13 g (0.1 mole) of 2-(E)-phenylmethylene-cyclohexane-1-one-(E)-oxime and 22.02 g (0.11 mole) of 1-diisopropylamino-2-chloro-ethane-hydrochloride are used as starting material. Thus 30.99 g of the desired compound are obtained, yield 94.3%. The 2-(E)-butenedioate (1/1) salt melts at 103°–104° C.

Analysis for the Formula $C_{25}H_{36}N_2O_5$ (444.58): calc.: C %=67.54, H %=8.16, N %=6.30; found: C %=67.54, H %=8.34, N %=6.34.

U.V.: $\lambda_{max}$=275 nm ($\epsilon$=17304)

EXAMPLE 13

Preparation of
2-[(E)-(p-chloro-phenylmethylene)]-1-]-1-[(E)-(2'-dimethylamino-ethoxyimino)]-cyclohexane One proceeds according to Example 1 except that 23.57 g (0.1 mole) of 2-[(E)-(p-chloro-phenylmethylene)]-cyclohexane-1-one-(E)-oxime and 12.24 g (0.105 mole) of 1-dimethylamino-2-chloro-ethane are used as starting material. Thus 28.60 g of the desired compound are obtained, yield 93.2%. The 2-(E)-butenedioate (1/1) melts at 169°–171° C.

Analysis for the Formula $C_{21}H_{27}ClN_2O_5$ (422.92): calc.: C %=59.64, H %=6.44, Cl %=8.38, N %=6.62; found: C %=59.42, H %=6.38, Cl %=8.27, N %=6.67.

U.V.: $\lambda_{max}$=275 nm ($\epsilon$=19292)

What we claim is:

1. A compound of the formula I

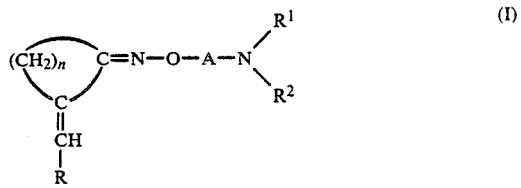

wherein, n is 4;

R is phenyl or 4-chloro-phenyl;

A is trimethylene; and $R^1$ and $R^2$ each stand for isopropyl, said compound having an E,E-configuration, and pharmaceutically acceptable acid addition salts thereof.

2. A method of combating angina in a patient suffering therefrom which comprises: treating said patient with a pharmaceutical composition containing an effective amount of a compound of the formula I as defined in claim 1.

3. 2-[(E)-(p-chloro-phenylmethylene)]-1-[(E)-(3'-diisopropylamino-propoxyimino)]-cyclohexane and pharmaceutically acceptable acid addition salts thereof.

4. 2-[(E)-phenylmethylene]-1-[(E)-(3'-diisopropylamino-propoxyimino)]-cyclohexane and pharmaceutically acceptable acid addition salts thereof.

5. A method of combating angina in a patient suffering therefrom which comprises: treating said patient with a pharmaceutical composition containing an effective amount of a compound of the formula (I)

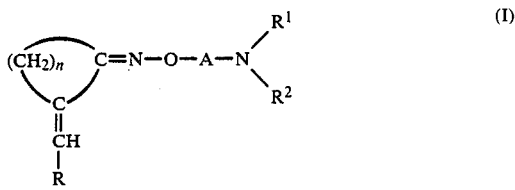

wherein n is 4–6 and when n is 4,

R stands for phenyl, A is trimethyllene and $R^1$ and $R^2$ each stand for isopropyl or together with the adjacent nitrogen atom form a N-phenyl-piperazine group; or R stands for phenyl, A is ethylene and $R^1$ and $R^2$ each stand for isopropyl; or R stands for phenyl, A is —$CH_2$—$CH(CH_3)$— and $R^1$ and $R^2$ each stand for methyl; or R stands for 4-chloro-phenyl, A is trimethylene and $R^1$ and $R^2$ each represent isopropyl; or R stand for 4-chloro-phenyl, A is ethylene and $R^1$ and $R^2$ each stand for methyl; or when n is 5, R stands for phenyl, A is ethylene and $R^1$ and $R^2$ are identical and each stand for methyl or isopropyl; or R stands for phenyl, A is —$CH_2$—$CH(CH_3)$— and $R^1$ and $R^2$ are methyl; or R stands for 3-chloro-phenyl, A is trimethylene and $R^1$ and $R^2$ together with the adjacent nitrogen atom form a N-benzylpiperazine group; or when n is 6, R stands for phenyl, A is trimethylene and $R^1$ and $R^2$ each stand for methyl; or R stands for phenyl, A is ethylene and $R^1$ and $R^2$ each stand for isopropyl;
with the proviso that when n is 5 and R is phenyl and A is ethylene and $R^1$ and $R^2$ each are isopropyl, the compound of the general formula (I) is of Z,E configuration and in all the other cases the compound of the formula (I) is of E,E-configuration, and pharmaceutically acceptable acid addition salts thereof.

6. The method of claim 5, wherein the patient is administered a daily dose of the compound of Formula (I) in the amount of 0.25 to 40 mg/kg.

* * * * *